United States Patent [19]

Van Der Puy et al.

[11] Patent Number: 4,786,733

[45] Date of Patent: Nov. 22, 1988

[54] DIRECT FLUORINATION OF SUBSTITUTED PYRIDINES

[75] Inventors: Michael Van Der Puy, Cheektowaga; Richard E. Eibeck, Orchard Park, both of N.Y.

[73] Assignee: Allied-Signal Inc., Morris Township, Morris County, N.J.

[21] Appl. No.: 71,233

[22] Filed: Jul. 9, 1987

[51] Int. Cl.$^4$ .................. C07D 213/72; C07D 213/24; C07D 213/04; C07D 213/30

[52] U.S. Cl. .................................... 546/286; 546/298; 546/303; 546/314; 546/315; 546/340; 546/345

[58] Field of Search ............... 546/286, 303, 298, 314, 546/315, 340, 345

[56] References Cited

U.S. PATENT DOCUMENTS

| | | | |
|---|---|---|---|
| 2,447,717 | 8/1948 | Simons | 260/539 |
| 4,493,932 | 1/1985 | Werner | 546/345 |
| 4,546,192 | 10/1985 | Fujioka et al. | 546/345 |
| 4,567,274 | 1/1986 | Gatlin et al. | 546/345 |

FOREIGN PATENT DOCUMENTS 0206564 12/1983 Japan .................... 546/345

OTHER PUBLICATIONS

Boudakian, *J. Heterocyclic Chem.*, 1967, 4, 381.
Finger and Starr, *J. Am. Chem. Soc.*, vol. 81, pp. 2674–2675.
MeBee, *Ind. Eng. Chem.*, 1947, 39, 389.
Mosher, *Heterocyclic Compounds*, vol. I. ed. R. C. Elderfield, Chapter 8, p. 509, John Wiley, 1950.
Meinert, H. *Z. Chem.*, 3, Jg. (1965).

*Primary Examiner*—Mary C. Lee
*Assistant Examiner*—J. Richter
*Attorney, Agent, or Firm*—Jay P. Friedenson; Harold N. Wells

[57] ABSTRACT

Substituted pyridine compounds particularly alkyl-substituted pyridines, are directly fluorinated to the corresponding 2-fluoro alkyl-substituted pyridines. Fluorine gas, preferably diluted with an inert gas, is passed into the substituted pyridine, preferably in a solvent, at a temperature of +25° C. to −40° C., preferably about −25° C.

18 Claims, No Drawings

DIRECT FLUORINATION OF SUBSTITUTED PYRIDINES

FIELD OF INVENTION

The invention is related generally to the direct fluorination of organic compounds and more particularly to the direct fluorination of substituted pyridines, especially alkyl pyridines.

BACKGROUND OF THE INVENTION

Direct fluorination of organic compounds must be carried out under suitable conditions to control the aggressive reaction of elemental fluorine. The present invention is directed to the placing of elemental fluorine in the 2-ring position of substituted pyridines.

Simons (U.S. Pat. No. 2,447,717) recommended pyridine as a reaction medium for direct fluorination of various organic compounds, including toluene, benzene, acetic acid and others. He speculated that fluorine complexes with pyridine and becomes a fluorinating agent for other organic compounds. Simons does indicate that pyridine can form 2-fluoropyridine when no other organic compound is present. Methyl pyridine is mentioned as an alternative material which can be used as a reaction medium, but direct fluorination of that compound is not discussed.

Alkyl substituted pyridines can be fluorinated in the 2-ring position by replacing another substituent already located there. The Schiemann reaction replaces an amino group at the 2-ring position with a fluorine atom. Another approach begins with a chlorine atom at the 2-ring posirion and replaces it with fluorine supplied by $KHF_2$ according to Boudakian, *J. Heterocyclic Chem.*. 1967, 4,381 or by NaF according to Finger and Starr, *J. Am Chem Soc*, Vol. 81, pp. 2674-2675.

The direct fluorination of alkyl-substituted pyridines has not been given much attention in the art. The corresponding reaction of chlorine with alkyl pyridines has been studied by McBee (Ind. Eng. Chem., 1947, 39, 389 and others). When an alkyl group is present, it is chlorinated first and only when rigorous conditions are employed is chlorine introduced into the ring. Thus, while chlorine will react with pyridine to give 2-chloropyridine, if methyl pyridine is used, the product is trichloromethyl pyridine. As will be seen, these results are in striking contrast with the results obtained in the fluorination of alkyl pyridines.

More generally, the halogenation of pyridines has been discussed by Mosher in *Heterocyclic Compounds*, Vol. I, ed R. C. Elderfield, Chap. 8, p. 509, John Wiley, 1950. Mosher states that while pyridine derivatives with ortho or para-directing groups (i.e. $OCOCH_3, NHR$) have been directly substituted, that where meta-directing groups (i.e. CN, COOR, COR, NO ) are present, halogenation is not expected. As previously discussed, Mosher indicates that with the picolines chlorine reacts with the methyl group and not with the nucleus until the methyl group has been fully chlorinated. From this discussion, one skilled in the art could expect that fluorine would not react with the nucleus and instead would prefer to react with alkyl substituted groups.

Since 2-fluoro pyridines are useful chemical intermediates, it would be desirable to be able to directly fluorinate substituted pyridines in the 2-ring position. Unexpectedly, the present inventors have found that under mild reaction conditions such a reaction is possible.

SUMMARY OF INVENTION

Substituted pyridine compounds are directly fluorinated to form the corresponding 2-fluoro substituted pyridine The pyridines may be substituted with $C_1$ to $C_8$ alkyl. aralkyl, aryl, Cl, acetyl, carbomethoxy, or cyano groups. The reaction may be carried out in the presence of an inert solvent such as trichlorotrifluoroethane. The temperature may be from 25° C. to −40° C., but lower temperatures, preferably about −25° C. are preferred. The fluorine usually will be diluted with an inert gas such as nitrogen to provide a mixture containing about 5 to 20 volume percent fluorine. The process of the invention is relatively simple and avoids the use of starting materials which have other substituents in the 2-ring position.

DESCRIPTION OF THE PREFERRED EMBODIMENTS

Although it might be expected that substituted pyridines would be fluorinated at the substituted group, it has been found instead that fluorination occurs at the 2-ring position. In view of the aggressive nature of fluorine the direct fluorination of the ring instead of the alkyl substituents was unexpected.

The reaction may be carried out with various substituted pyridines, particularly including those represented by the formula

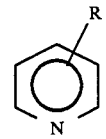

where R is $C_1$ to $C_8$ alkyl, aralkyl, aryl, Cl, acetyl, carbomethoxy, cyano

Since the fluorine atom is placed on the ring, hydrogen is displaced and hydrogen fluoride is produced as a by-product. Hydrogen fluoride may be scavenged by the use of an excess of the pyridine compound.

An advantage for the present process is that substituted pyridines are readily available at lower cost than the starting materials used for reactions which displace another substituent from the 2-ring position.

The reaction is relatively simple to carry out since the substituted pyridine may be placed in a vessel, preferably mixed with an inert solvent, and fluorine gas is bubbled into the mixture at a temperature of +25° C. to −40° C. preferably below 0° C., most preferably about −25° C. Usually the fluorine gas will be diluted with an inert gas such as nitrogen in order to moderate the aggressive reaction of elemental fluorine. Mixtures containing 5-20 volume percent fluorine are suitable. with about 10 volume percent being preferred.

The presence of a solvent is preferred since it appears to improve the yield of the 2-fluoro pyridine obtained. The solvent should be substantially inert to fluorine gas and therefore. such solvents preferably are a fully chlorinated or fluorinated hydrocarbon, such as fluorotrichloromethane and trichlorotrifluoroethane. However, other solvents have been found useful, including chloroform and acetonitrile. Preferably, the amount of solvent will be about 50-90 volume percent of the combined pyridine and solvent.

In the following examples substituted pyridine is placed in a stirred glass reactor along with a solvent and fluorinated by passing a diluted fluorine gas into the mixture, while maintaining a desired temperature using a cooling bath. At the end of the reaction period diethyl ether was added to the mixture and the remaining pyridine was extracted with aqueous HCl and the 2-fluoro pyridine recovered from the ether phase.

EXAMPLE 1

2-Fluoro-4-methylpyridine

To a solution of 10.1 g (0.109 mol) 4-methylpyridine in 30 mL $CF_2ClCFCl_2$ at 0° C. was added $F_2$ (8 cc/min) diluted with $N_2$ (72 cc/min) for a period of 3 hours (total $F_2$ was 56 mmol). After flushing the apparatus with $N_2$ and warming to room temperature. 100 mL ether was added. The organic layer was extracted with 1N HCl and dried with $Na_2SO_4$. After removing the volatiles under reduced pressure, there was obtained 1.5 g light amber oil, homogeneous by GC. identified as 2-fluoro-4-methylpyridine by comparison of its spectral properties with authentic material purchased commercially. The yield, based on $F_2$ added, was 24%.

EXAMPLE 2

2-Fluoro-3-methylpyridine and 2-Fluoro-5-methylpyridine

Ten grams 3-methylpyridine (0.108 mol) and 15 mL $CF_2ClCCl_2F$ were cooled to $-25°$ C. A mixture of $F_2$ (8 cc/min) in $N_2$ (68 cc/min) was bubbled under the surface of the solution for 3 hours (total $F_2$ was 56 mmol). At the end of the reactlon two phases were present. Ether (125 mL) was added. and the resultant ether phase was decanted into a separatory funnel, leaving most of the dark, insoluble oily phase behind. The ether solution was washed with water (50 mL). 1N HCl (100 mL and 25 mL). saturated NaCl solution (25 mL) and dried with $MgSO_4$. Rotary evaporation of the ether provided 2.7 g amber oil identified (by comparison with material purchased commercially) as a mixture of 2-fluoro-3-methylpyridine (28% yield based on $F_2$) and 2-fluoro-5-methylpyridine (15% yield) for a total yield of 43%.

EXAMPLE 3

2-Fluoro-4-ethyl pvridine

4-Ethylpyridine (15.2 g: 0.142 mol) in 22 mL $CF_2ClCCl_2F$ was cooled to $-25°$ C. A mixture of $F_2$ (8 cc/min) and $N_2$ (68 cc/min) was bubbled into this solution for 4 hours (total $F_2$ was 74.8 mmol). After this time. the mixture was diluted with ether and extracted with 1N HCl. Rotary evaporation of the dried ether phase gave 3.0 g of an oil identified as 2-fluoro-4-ethylpyridine on the basis of its NMR spectrum which had a splitting pattern in the aromatic region the same as that for 2-fluoro-4-methylpyridine. The yield based on $F_2$ was 32%. BP 79°–81° C. at 22 mm. NMR($CDCl_3$) 8.07 (d, 1H). 7.0 (distorted d, 1H). 6.7 (s, 1H), 2.67 (q, 2H), 1.25 (t, 3H).

EXAMPLE 4

2-Fluoro-3,5-dimethylpyridine

A solution of 19.6g 3,5-lutidine in 20 mL $CCl_2FCF_2Cl$ was cooled to 0° C. Fluorine (8 cc/min) diluted with $N_2$ (80 cc/min) was bubbled in for 3.5 hours (total $F_2$ was 65 mmol). During this time a precipitate formed. Work-up consisted of adding 150 mL ether and washing the organic phase with water (100 mL). 1N HCl (100 mL) and saturated brine (50 mL).

After drying ($Na_2SO_4$). the volatiles were removed by rotary evaporation to give 3.0 g (37% based on $F_2$) oil identified as 2-fluoro-3,5-dimethylpyridine. Bp 85°86° C. at 26 mm. NMR ($CDCl_3$) δ7.8 (bs, 1H). 7.45 (dd, 1H). 2.28, 2.25 (6H).

EXAMPLE 5

2-Fluoro-6-methylpyridine

A mixture of $F_2$ (8 cc/min) and $N_2$ (68 cc/min) was added for 4.5 hours (84 mmol $F_2$) to a solution of 19.1 g 2-picoline in 30 mL $CF_2ClCCl_2F$ at $-25°$ C. Recovery using the method of Example 1 provided 0.9 g liquid. the major component of which was identified as 2-fluoro-6-methyl pyridine by co-injection on the gas chromatograph with authentic material purchased commercially. The yield was about 6%.

EXAMPLE 6

2-Fluoro-4-benzylpyridine

A solution of 25.0 g 4-benzylpyridine in 20 mL $CF_2ClCCl_2F$ was cooled to $-25°$ C. $F_2$ (8 cc/min) diluted with $N_2$ (68 cc/min) was bubbled in subsurface for 3h (56 mmol $F_2$). The reaction mixture was allowed to warm to room temperature and 150 mL ether added. The organic layer was washed with water, 1N HCl, and brine. After drying. the ether and $CF_2ClCCl_2F$ were removed by rotary evaporation to give 2.6 g (25% yield) amber oil (95% pure by GC) identified as 2-fluoro-4-benzylpyridine. Bp 77° C. at 0.05 mm; NMR ($CDCl_3$)δ8.1 (d, 1H). 7.4–7.1 (m, 5H). 6.97 (distorted d, 1H), 6.7 (s, 1H). 3.96 (s, 2H). Analysis as calculated for $C_{12}H_{10}FN$:C, 76.96%; H, 5.38%; N, 7.51%; by measurement C, 76.71%; H, 5.45%; N, 7.42%.

EXAMPLE 7

2-Fluoro-4-isopropylpyridine

4-Isopropyl pyridine (18.1 g) was dissolved in 21 mL $CF_2ClCFCl_2$ and cooled to $-40°$ C. $F_2$ (8 cc/min) diluted with $N_2$ (80 cc/min) was bubbled in. After 50 min. at $-40°$ C., the solution was warmed to $-25°$ C. ($F_2$ exiting reactor) and the temperature maintained at $-25°$ C. for an additional 160 min. while continuing to add $F_2/N_2$ (65 mmol $F_2$ total). The reaction mixture was allowed to warm to room temperature, but during this warming period, a modest exotherm resulted, apparently from solid material on the inlet tube near the liquid surface. An additional 50 mL $CF_2ClCCl_2F$ was added, and the organic layer was washed with 50 mL water, 50 mL 1N HCl, and 50 mL water. After drying with $Na_2SO_4$ the solvent was removed to give 4.3 g liquid (47% yield based on F added) which was identified as 2-fluoro-4-isopropylpyridine, bP 75° C. at 15 mm. NMR ($CDCl_3$) 8.12 (d, 1H). 7.16 (distorted d, 1H), 6.75(s, 1H). 2.92 (heptet. 1H). 1.25 (d, 6H).

EXAMPLE 8

The effect of temperature and solvent on the yield of 2-fluoro-4-methylpyridine from 4-picoline is shown in the table below. In each case 10% $F_2$ in $N_2$ was bubbled into the reaction medium. Yields are based on total $F_2$ added.

| 4-Picoline (g) | $CF_2ClCFCl_2$ (mL) | Temp | Yield |
| --- | --- | --- | --- |
| 19.4 | 0 | 0° C. | 10% |
| 19.4 | 0 | $-25°$ C. | 16% |
| 10.1 | 30 | 0° C. | 24% |

| 4-Picoline (g) | CF$_2$ClCFCl$_2$ (mL) | Temp | Yield |
| --- | --- | --- | --- |
| 10.1 | 30 | −25° C. | 31% |

In each case the yield was higher when solvent was present and the yield was increased at the lower temperature.

EXAMPLE 9

2-Fluoro-3, 5-dichloropyridine 3, 5-dichloropyridine (27.5 g) was dissolved in 130 mL of trichlorotrifluoroethane. Fluorine (8 cc/min) diluted with nitrogen (75 cc/min) was bubbled into the solution at room temperature for three hours to provide a total of 56 mmol of fluorine, while adding fresh solvent as required to maintain the original volume. The reaction mixture was washed five times with 100 mL portions of 4N HCl. dried over Na$_2$SO$_4$. and the solvent evaporated under reduced pressure. A light yellow solid (7.4 g) was recovered, which was sublimed to yield 4.3 g of a white solid. Recrystallization from petroleum ether produced a pure product having a melting point of 41°–42° C.

EXAMPLE 10

2-Fluoro-4-carbomethoxy pyridine

Methyl isonicotinate (25.5 g) was dissolved in 125 mL trichlorotrifluoroethane and cooled in an ice bath (i.e. 0° C.) Fluorine (8 cc/min) diluted with nitrogen (80 cc/min) was bubbled through the solution for 4 hours until a total of 75 mmol fluorine had been added. The reaction mixture was allowed to warm to room temperature and then washed with 100 mL portions of water, 2N HCl. and water, and then dried with Na$_2$ SO$_4$ A small amount of a third phase formed during the extraction was removed by filtration and discarded. A liquid product (7.1 g) was obtained. Distillation of the liquid produced 5.3 g of product having a boiling point of 82°–85° C. at 8 mm Hg absolute pressure. The results of analyses confirmed the presence of 2-fluoro-4-carbomethoxy pyridine as follows:

IR (neat): 1745 cm$^{-1}$ (C=0).
NMR (CDCl$_3$): 8.35 (d, J=5 Hz. 1H), 7.73 (m, 1H), 7.47 (d, J=1–2 Hz, 1H), 3.98 (S. 3H).
MS m/z 155: (parent). 124 (base)

EXAMPLE 11

2-fluoro-3-carbomethoxy pyridine and 2-fluoro-5-carbomethoxy pyridine

Methyl nicotinate (25 g) was dissolved in carbon tetrachloride and cooled in an ice bath to 0° C. Fluorine (8 cc/min) diluted with nitrogen (68 cc/min) was bubbled through the solution for 4 hours until 72 mmol of fluorine had been added. The reaction mixture was allowed to warm to room temperature and then 100 mL of water was added. The resulting mixture was phase-separated. The aqueous fraction was extracted with 50 mL of carbon tetrachloride and the extractant combined with the organic phase and then washed twice with 100 mL 3N HCl and once with water. The washed organic phase was dried with Na$_2$SO$_4$ and then evaporated to yield 5.2 g of a solid. The solid was treated with 25 mL of trichlorotrifluoroethane and filtered to remove impurities. leaving 3.8 g of a 55/45 mixture of 2-fluoro-5-carbomethoxy pyridine and 2-fluoro-3-carbomethoxy pyridine as determined by 19 F and 1H NMR. 2-F-5 COOCH$_3$, δ8.9 (d, J=2 Hz, H6), 8.3–8.6 (H4). 6.95 (dd, J=2 and 9 Hz, H3). 2-F-3 COOCH$_3$, 8.3–8.6 (H4 and H6), 7.2–7.4 (H5).

EXAMPLE 12

2-fluoro-4-acetyl pyridine

In a manner similar to that described in Example 9, 75 mmol of fluorine diluted with nitrogen was added over a 4 hour period to a solution of 24.4 g 4-acetyl pyridine in 125 mL of trichlorotrifluoroethane maintained at 0° C. The product was recovered using the method described in Example 10 to yield 3 3. g of crude product. Recrystallization from petroleum ether gave 2.7 g of a pale yellow solid and sublimation produced a pure white solid having a melting point of 37.5°–39° C. The presence of 2-fluoro-4-acetyl pyridine was confirmed by the following analytical results:

IR (nujol null): 1710 cm$^{-1}$ (C=0);
NMR (CDCl$_3$)δ8.43 (d, 1H). 7.65(m. 1H), 7.40 (bs, 1H). 2.67 (s, 3H).
Elemental analysis: Calculated: C, 60.43; H, 4.35; N, 10.07. Measured: C, 60.34; H, 4.38; N, 9.91.

We claim:

1. A process for producing 2-fluoro substituted pyridine compounds comprising contacting a pyridine compound selected from the group consisting of pyridines substituted with C$_1$ to C$_8$ alkyl, aralkyl, aryl, Cl, acetyl, carbomethoxy. and cyano with diluted gaseous fluorine at a temperature of +25° to −40° C.

2. The process of claim 1 wherein the gaseous fluorine is diluted with an inert gas.

3. The process of claim 2 wherein the inert gas is nitrogen.

4. The process of claim 1 wherein the reaction is carried out in a suitable solvent.

5. The process of claim 4 wherein said solvent is completely fluorinated or chlorinated hydrocarbon.

6. The process of claim 5 wherein the solvent is trichlorotrifluoroethane.

7. The process of claim 4 wherein said solvent is chloroform or acetonitrile.

8. The process of claim 1 wherein said temperature is 0° to −40° C.

9. The process of claim 8 wherein said temperature is about −25° C.

10. The process of claim 4 wherein the amount of solvent is 50 to 90 volume percent of the combined pyridine and solvent.

11. The process of claim 2 wherein the amount of fluorine is 5 to 20 volume percent of the combined fluorine and inert gas.

12. The process of claim 1 wherein the pyridine is substituted with a C$_1$ to C$_8$ alkyl group.

13. The process of claim 1 wherein the pyridine is substituted with an aralkyl group.

14. The process of claim 1 wherein the pyridine is substituted with an aryl group.

15. The process of claim 1 wherein the pyridine is substituted with chlorine.

16. The process of claim 1 wherein the pyridine is substituted with an acetyl group.

17. The process of claim 1 wherein the pyridine is substituted with an carbomethoxy group.

18. The process of claim 1 wherein the pyridine is substituted with a cyano group.

* * * * *